United States Patent [19]
Young

[11] Patent Number: 5,871,497
[45] Date of Patent: Feb. 16, 1999

[54] COMBINATION DISSECTOR AND EXPANDER

[75] Inventor: Roderick A. Young, Palo Alto, Calif.

[73] Assignee: General Surgical Innovations, Inc., Cupertino, Calif.

[21] Appl. No.: 999,337

[22] Filed: Dec. 29, 1997

Related U.S. Application Data

[62] Division of Ser. No. 726,072, Oct. 3, 1996, Pat. No. 5,776,159.

[51] Int. Cl.⁶ ..................................................... A61B 17/00
[52] U.S. Cl. ................................................. 606/190; 623/8
[58] Field of Search ................................. 606/190; 623/8, 623/7; 128/898

[56] References Cited

U.S. PATENT DOCUMENTS

| | | | |
|---|---|---|---|
| 4,615,704 | 10/1986 | Frisch | 623/8 |
| 4,624,671 | 11/1986 | Kress | 623/8 |
| 4,701,230 | 10/1987 | Loi | 156/145 |
| 5,026,394 | 6/1991 | Baker | 623/8 |
| 5,147,398 | 9/1992 | Lynn et al. | 623/8 |
| 5,258,026 | 11/1993 | Johnson et al. | 623/8 |
| 5,331,975 | 7/1994 | Bonutti | 128/898 |
| 5,411,554 | 5/1995 | Scopelianos et al. | 128/898 |
| 5,496,345 | 3/1996 | Kieturakis et al. | 606/192 |
| 5,500,019 | 3/1996 | Johnson et al. | 623/8 |
| 5,514,153 | 5/1996 | Bonutti | 606/190 |
| 5,655,545 | 8/1997 | Johnson et al. | 128/898 |
| 5,658,328 | 8/1997 | Johnson | 128/898 |

*Primary Examiner*—Michael Buiz
*Assistant Examiner*—Kevin Truong
*Attorney, Agent, or Firm*—Lyon & Lyon LLP

[57] ABSTRACT

A combination tissue dissector and long term expander is disclosed for use in plastic surgery applications and other applications where it is desirable to dissect a tissue pocket and serially expand the dissected pocket through long term tissue expansion. The combination device performs the separate functions of dissection and long term expansion in a single balloon package. In an exemplary embodiment, three sheets of substantially inelastic material are bonded together at their outer margins to form two discrete inflatable chambers. The lower inflatable chamber defined by the middle and lower balloon sheets is further welded together at various points over the sheet's surface area to create a semi-rigid base portion which provides a flat well-defined footprint for the balloon. The semi-rigid base prevents further enlargement of the tissue pocket at the margins when the device is utilized as a tissue expander. In a preferred method of use for the combination device, the combination device is tunneled bluntly to a desired location within the body. The device is then inflated to dissect tissue layers along natural tissue planes and create a tissue pocket. After dissection, the combination device may be left within the body as a temporary implant to further expand the tissue pocket through long term expansion until the desired tissue pocket volume is achieved.

7 Claims, 4 Drawing Sheets

COMBINATION DISSECTOR AND EXPANDER

This is a divisional of U.S. application Ser. No. 08/726,072, filed on Oct. 3, 1996 now U.S. Pat. No. 5,776,159. The priority of the prior application is expressly claimed, and the disclosure the prior application is hereby incorporated by reference in its entirety.

FIELD OF THE INVENTION

The present invention pertains generally to the field of surgical apparatus and methods for use in creating an anatomic working space and thereafter expanding the space. More particularly, the present invention pertains to an inflatable balloon dissector and its methods of use wherein a single balloon device combines the function of tissue dissection with long term tissue expansion.

BACKGROUND OF THE INVENTION

In the past, inflatable devices have been utilized to dissect tissue layers to create an anatomic working space to facilitate the performance of laparoscopic or other minimally invasive surgical procedures. For example, in commonly assigned U.S. Pat. No. 5,514,153 to Peter M. Bonutti, the disclosure of which is hereby incorporated by reference in its entirety, various inflatable devices are disclosed which can be utilized to dissect tissue to create an anatomic working space. A surgical balloon dissector and its methods of use are also disclosed in commonly assigned U.S. Pat. No. 5,496,345, to Kieturakis et al., the disclosure of which is also hereby incorporated by reference in its entirety. It has been found that a tissue pocket formed by balloon dissection is generally more regular and precise than the pocket typically obtained with manual dissection. In contrast to traditional blunt dissection techniques, the dissecting balloon creates a tissue pocket while respecting natural tissue planes or boundaries in the anatomy.

A second class of inflatable devices known as tissue expanders are fluid operated devices which, when inflated, stretch and place pressure on overlying tissues to create tissue growth in a localized area of the body. Tissue expanders have generally been used in plastic or reconstructive surgery as temporary implants to gradually expand a previously dissected pocket over time as the overlying skin and tissue gradually alters (through new cell formation) and expands in response to the force applied by the inflatable tissue expander. Often, the "created" tissue is stretched over an adjacent area where a tissue defect has been removed or where additional tissue is required. Tissue expanders traditionally incorporate inflation ports which are connected by an inflation tube to the expander and are implanted somewhat remote from the expansion site. The inflation ports are small reservoirs which incorporate a self-sealing membrane through which fluid may be introduced by hypodermic needle. The port is placed under the skin such that there is easy needle access to the membrane.

In the conventional use of tissue expanders, it has been customary to make an incision immediately adjacent to or over the region into which the expander is to be subsequently placed, and then to utilize a blunt instrument or the finger to dissect exposed tissue layers to create a pocket. Generally, it is desirable to dissect the pocket adequately such that the dissected footprint easily accommodates the expander without curling the edges of the expander at the dissection margins. Once the expander is placed into the dissected space, the incision through which the dissection and expander placement was accomplished is closed and allowed to heal before the expansion process begins. This step is necessary because the tissue strength at the incision must be reestablished in order to withstand the stresses caused by long term tissue expansion. Otherwise, there is chance that the expander will extrude out of the incision preferentially to expanding the tissue over the dissected footprint, as desired. This healing step may require considerable time (on the order of weeks) before tissue expansion can begin.

Recently and commensurate with the trend toward minimally invasive surgery, practitioners have begun inserting tissue expanders into previously dissected pockets in the body through incisions remote from the expansion site such that the lengthy incision healing step can be eliminated. This advantageously allows expansion to be commenced immediately after placement of the tissue expander. Use of a remote insertion site also requires dissection to be accomplished through the remote incision and that the expanders are capable of being rolled or otherwise compacted to allow for proper placement at the remote site through the incision.

In the tissue expander art, it is also known that excessive inflation pressures in the tissue expander can cause tissue necrosis. Hence, the inflation pressure of the tissue expander must be moderated to avoid necrosis. Because the pressure must be held beneath the necrosis level, tissue expanders are left in place over a prolonged period of time to allow the subcutaneous tissues to gradually alter and expand. This requires monitoring and periodical adjustment of the fluid volume in the expander as the tissue gradually stretches over time.

In certain surgical procedures, especially in plastic surgery procedures, it is necessary to dissect a tissue pocket for the later implantation of a prosthetic device. For example, breast augmentation and reconstruction procedures involve dissecting a space or pocket in the breast and, if necessary, following the dissection step with long term tissue expansion to enlarge the pocket to receive the desired implant. Previously, two or more different devices have been required to perform the dissection and expansion steps.

Johnson et al., U.S. Pat. No. 5,258,026, discloses a surgical procedure for breast augmentation. In Johnson, an incision is made in the umbilicus and an elongate hollow tube carrying an inflatable prothesis is tunneled above the chest wall to a position behind the breast. The prothesis itself is then utilized as a tissue dissector by overinflating the prosthesis to 150% of its anticipated ultimate fill volume to create the breast pocket. The prothesis is then reduced in volume to its intended final volume and left in place. The umbilical incision is then closed and the surgery completed. While Johnson discloses the use of an inflatable member to create a tissue pocket in the breast for the purpose of augmentation, Johnson uses the implant itself to dissect and does not provide a device or method for further expanding the tissue pocket through long term expansion should the size of the initially dissected space be insufficient.

Accordingly, there is a need for an improved device and associated methods of use which incorporate the features of a tissue dissector and long term tissue expander in a single device to overcome the aforementioned disadvantages in the prior art.

SUMMARY OF THE INVENTION

The present invention provides a combination device wherein a common fluid operated bladder (or compound bladders) may perform the distinct functions of tissue dissection and long term tissue expansion in serial order. The present invention preferably utilizes a substantially inelastic balloon formed from a urethane material, for example, to dissect tissue layers to create a tissue pocket or working space, and thereafter to provide long term tissue expansion if desired.

A combination dissector/expander according to the invention may be any one of the balloon dissectors described in commonly assigned co-pending application Ser. No. 08/570,766, with appropriate modification to provide for an implantable self-sealing fill valve and provided that when the fluid volume is reduced appropriately after dissection, the balloon remains at a positive pressure. Suitable self-sealing valves which may be temporarily implanted (also known as injection ports) are known in the art and will not be described in detail herein. One example of a suitable self-sealing valve for use with a combination dissector/expander as disclosed herein is manufactured by CUI corporation, Santa Barbara, Calif., as part of a saline fill tissue expander. As disclosed in commonly assigned application Ser. No. 08/570,766, the disclosure of which is hereby incorporated by reference in its entirety, the balloon carried by the tunneling member is preferably rolled, folded or otherwise gathered about the tunneling member to provide a compact device. In several of the embodiments disclosed in application Ser. No. 08/570,766, provision is made for the use of a scope to permit observation within the body both as the device in tunneled to a desired location within the body where dissection is to occur and thereafter during balloon expansion as the tissue layers are dissected. For example, an internal scope cover can serve as a tunneling member, and could provide visualization during tunneling and/or dissection. However, in plastic surgery applications it is usually not necessary to provide for visualization because such operations are often performed in the physician's office rather than the hospital and visualization equipment, i.e., scopes and television monitors, are oftentimes unavailable.

A presently preferred combination dissector and expander is formed from three sheets of material bonded together at the outer margins of the sheets to form two discrete inflatable chambers. The top and middle sheets define a first inflatable chamber therebetween which is bonded at the common periphery of the sheets. The bottom and middle sheets are further bonded together at various points over their common surface area and define a separately inflatable semi-rigid chamber. Either chamber may be used as a tissue dissector, and the semi-rigid chamber provides a stable footprint for the device when it is utilized as a tissue expander to help avoid unwanted enlargement of the pocket at the dissection margins.

In a preferred method of use directed to plastic surgery applications, particularly breast augmentation and reconstruction, a combination fluid actuated dissector/expander is introduced, preferably by blunt tunneling, to a location where it is desired to create a tissue pocket. The balloon associated with the combination device is then inflated to dissect tissue layers and create the tissue pocket. After dissection, if the dissected pocket is not large enough to accommodate the desired prosthesis, the fluid volume (or pressure) of the combination device may then be adjusted to a level appropriate for long term tissue expansion. The combination tissue dissector/expander may be left in place over the amount of time required to achieve the desired amount of tissue expansion as is known in the tissue expander art, and the balloon fill volume (or pressure) adjusted over the period of time required to achieve gradual tissue expansion.

These and other aspects, features, objects, and advantages of the present invention will be more fully understood and appreciated upon consideration of the following detailed description of a preferred embodiment of the invention, presented in conjunction with the accompanying drawings wherein like reference numerals designate corresponding parts in the several figures.

DETAILED DESCRIPTION OF A PREFERRED EMBODIMENT

While principally described in terms of breast augmentation, the present invention may also be used in connection with other surgical procedures, including, but not limited to, brow lifts and scar tissue removal, for example.

Figure 1:
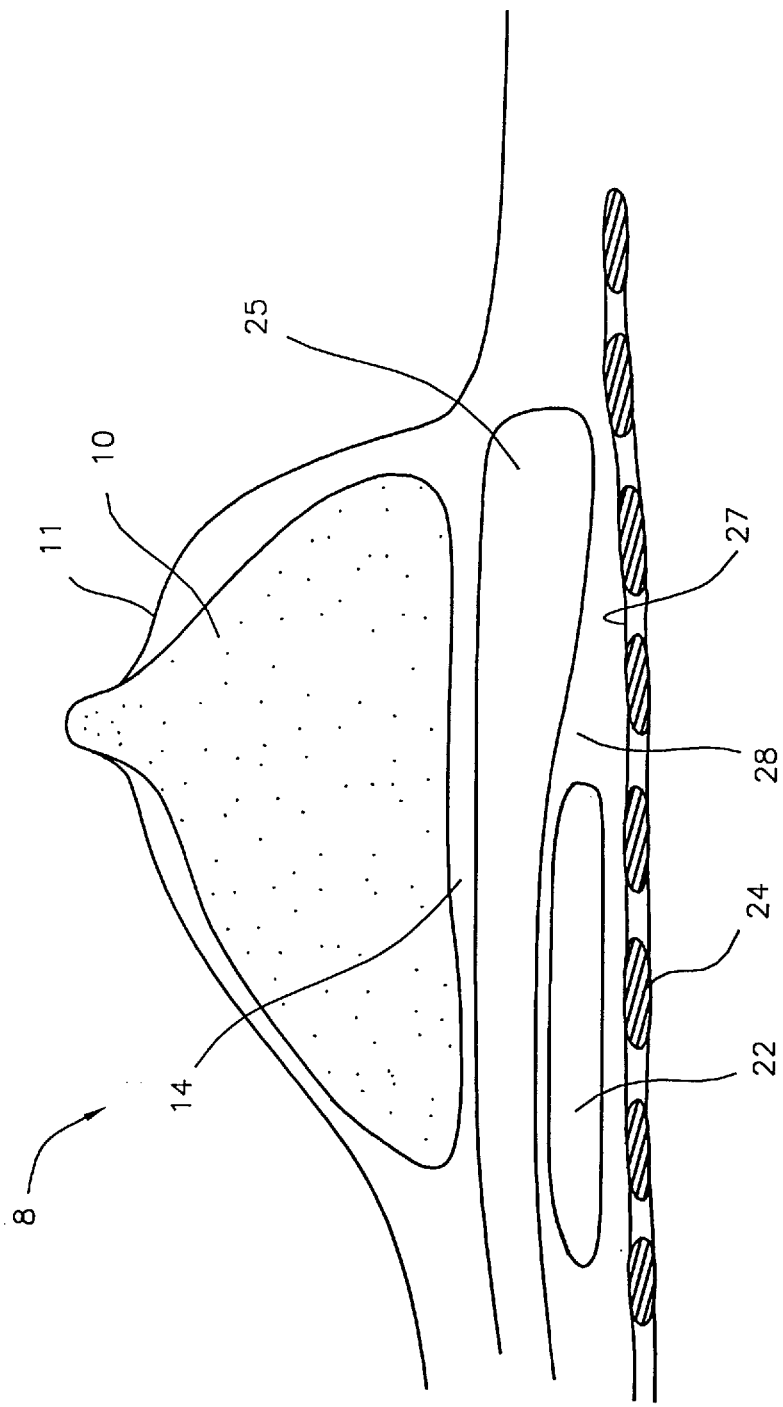
FIG. 1 is a cross-sectional view of the anatomy of the human breast including the subcutaneous layers down to the rib cage.

FIG. 1 illustrates a cross-sectional view of the anatomy of the human female breast 8. The breast 8 consists of a mound of glandular tissue 10 which is primarily fat. A layer of skin 11 covers the glandular tissue 10. The pectoralis major muscle 25 overlies the pectoralis minor muscle 22 and a portion of the chest wall 27 and ribs 24. A layer of pectoral fascia 14 lies between the overlying glandular breast tissue 10 and the pectoralis major muscle 25. The pectoral fascia 14 defines a naturally occurring tissue plane within the human body which may be bluntly dissected to create an anatomic working space or breast pocket. As discussed in application Ser. No. 08/570,766, balloon dissection along such naturally occurring tissue planes is desirable in that a virtually bloodless operating space may be created between the tissue planes.

Continuing with the description of the anatomy of the breast, a layer of deep pectoral fascia 28 sheaths the underside of the pectoralis major muscle 25 and separates the pectoralis major muscle 25 from the chest wall 27 and the pectoralis minor muscle 22. As will be explained below, like the pectoral fascia 14, the deep pectoral fascia 28 defines a naturally occurring tissue plane which may be bluntly dissected to create a tissue pocket between the pectoralis major muscle 25 and the chest wall 27.

In the general use of a combination dissector/expander, an incision is first made in the body at a location appropriate for the procedure and the combination device with a deflated balloon is tunneled bluntly to a desired location within the body as described in copending application Ser. No. 08/570,766, for example. In the case of breast augmentation or reconstruction, for example, several different incision sites may be appropriate depending on the surgical approach utilized.

Figure 2A:
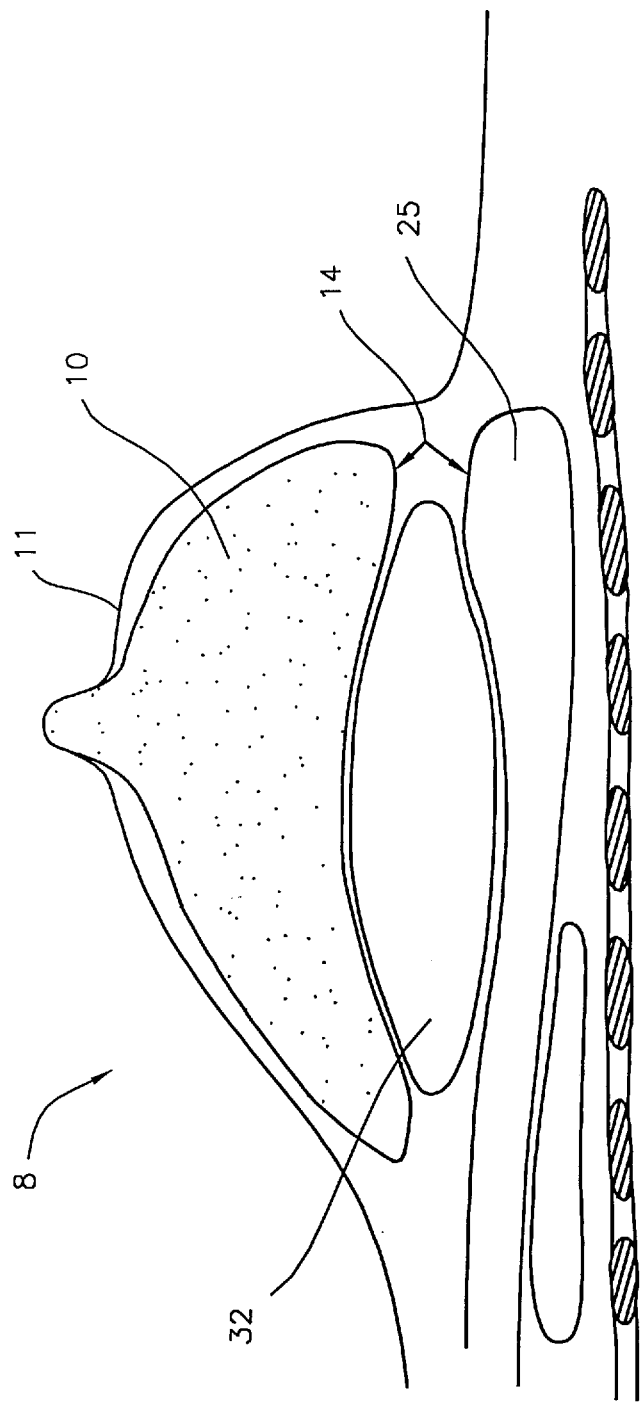
FIG. 2a is a cross-sectional view similar to FIG. 1 of the human breast illustrating a balloon in accordance with the present invention being utilized to form a tissue pocket between the pectoralis major muscle and glandular breast tissue.
Figure 2B:
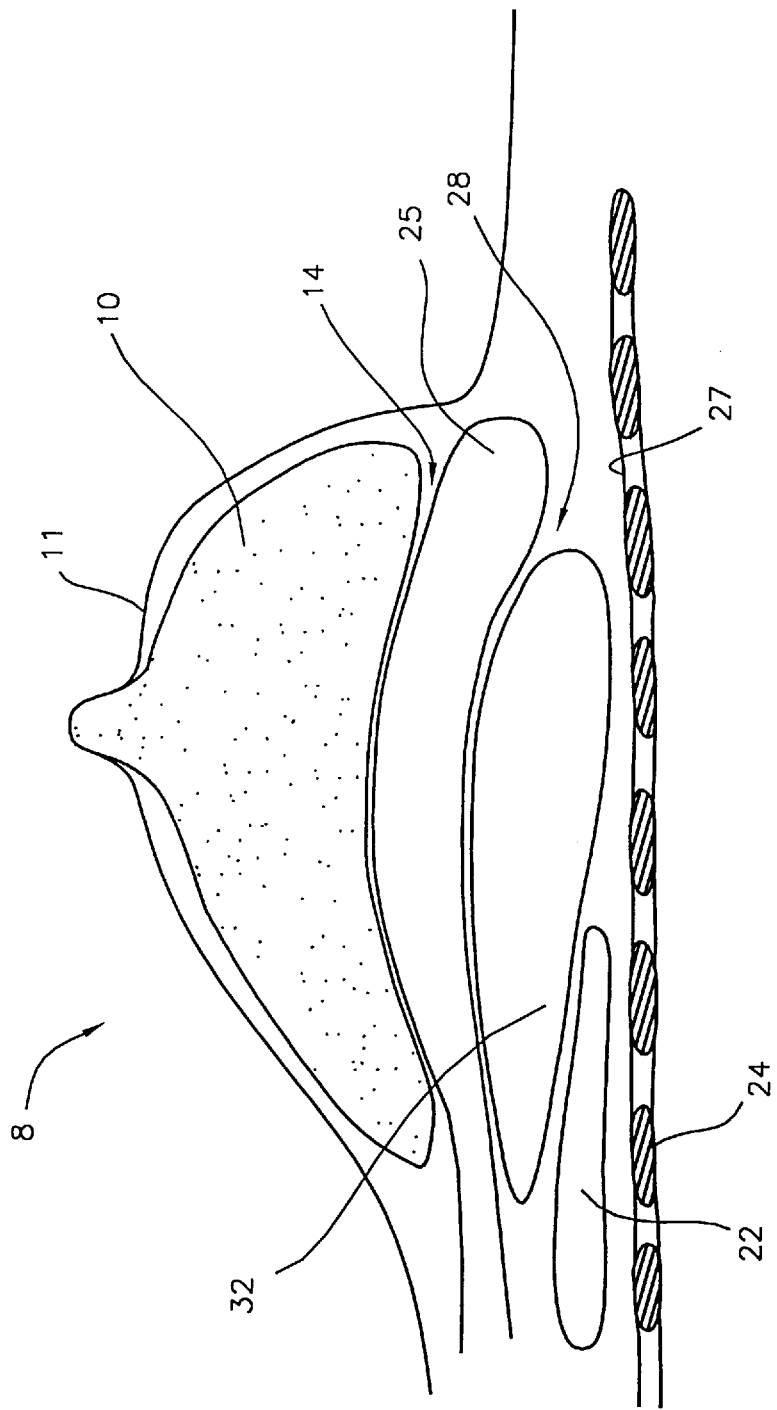
FIG. 2b is a view similar to FIG. 2a illustrating a balloon in accordance with the present invention being utilized to form a tissue pocket between the chest wall and the pectoralis major muscle overlying the chest wall.

A first approach in a breast augmentation procedure is to make an axillary incision and to utilize a combination device according to the invention to tunnel medially and inferiorly from the axillary incision to a desired location underlying the glandular breast tissue, either between the chest wall and pectoralis major muscle or between the pectoralis major muscle and the glandular breast tissue. When a subglandular implant is desired, the combination dissector/expander is preferably advanced along the layer of pectoral fascia 14, separating the layer in the process, until the balloon 32 associated with the device reaches the desired position beneath the glandular breast tissue 10. (See FIG. 2a). If a subpectoral implant is desired, a combination dissector/expander can be tunneled bluntly along the deep pectoral fascia layer 28 below the pectoralis major muscle 25 and above the chest wall 27 to the desired location as shown in FIG. 2b.

A second approach in breast augmentation is to access the breast tissue through the inframammary fold adjacent the breast. In this case, an inframammary incision is made and the combination device is tunneled superiorly into the breast tissue to a position behind the breast. In the case of a subglandular implant, the combination device is tunneled through the pectoral fascia 14, creating a small tunnel through the fascia 14, while in the case of a subpectoral implant, the combination device is tunneling through the deep pectoral fascia 28 between the chest wall and the pectoralis major muscle. (See FIGS. 2a and b).

A third approach is discussed in U.S. Pat. No. 5,258,026 to Johnson, the disclosure of which is hereby incorporated by reference in its entirety, where an incision is made in the umbilicus and the combination device is tunneled superiorly just above the fascia of the interior abdominal and chest wall and just below the subcutaneous tissue and fat. Upon approaching the breast pocket, the surgeon will have the choice of staying either above the chest muscle and tunneling between the chest muscle and the gland in the case of a subglandular implant or under the chest muscle and going between the chest muscle and the chest wall in the case of a subpectoral implant.

Whichever approach is chosen from the standpoint of incision entry point, after the deflated balloon has been properly positioned in either the subglandular or subpectoral position, the balloon is inflated by introducing a suitable inflation medium, such as saline solution for example, through a balloon inflation lumen into the interior of the balloon. The balloon is filled with a sufficient volume of fluid to cause the balloon to dissect tissue layers and create the desired pocket for the implant.

Although some level of intra-operative expansion may be accomplished by further short term expansion of the balloon at pressures exceeding the venous pressure, this is undesirable for several reasons. First, exceeding the venous pressure for an extended period may collapse the venous system as previously described. Second, intra-operative expansion may result in further tissue dissection at the margins of the dissected space, resulting in unwanted enlargement of the dissection footprint rather than further expansion in the anterior or Z-axis direction. During the long term tissue expansion step, it is desirable to monitor the pressure of the balloon to ensure that the internal pressure does not exceed about 18 millimeters of mercury, as pressures in excess of this range may collapse the venous system, possibly leading to tissue necrosis. To an extent, necrosis may be avoided by observing the physical appearance of the tissue involved. In contrast, the pressures required for dissection generally need not adhere to these limits because dissection occurs over a very limited time and may exceed the venous collapse limits by a considerable amount, depending on the dissection task. As a result of these greater pressures, some immediate tissue expansion and intraoperative tissue stretching may occur. The present invention is not directed to such immediate tissue expansion, but rather to the combination of dissection and long term tissue expansion.

It is to be noted that with traditional tissue expanders, an incision overlying the tissues to be expanded is made to insert the expander and then after the expander is inserted, the incision must be allowed to heal to prevent the incision from being reopened by the force of the tissue expander. In contrast, the preferred combination device may be tunneled in from a remote incision to a desired location where tissue expansion is to occur. This allows immediate tissue dissection of the pocket and then immediate initiation of expansion without the need to remotely form a pocket or to permit a local incision to heal.

Several balloon constructions are useful in the design of combination dissector/expander devices. Generally, it is useful to keep one side of the balloon relatively flat as it is gradually inflated, with the bulk of the expansion occurring to only one side. An illustrative example might be expanding tissue which overlies the rib cage for purposes of reconstructing a breast. This sort of balloon behavior requires nonuniform inflation characteristics. One embodiment of the combination device may incorporate different thicknesses on balloon material to control relative stretching and hence shape. In a balloon constructed of two flat sheets of the same material welded at their periphery, one sheet might be thicker, for example. In this case, progressive inflation would stretch the thinner sheet preferentially. Different materials, i.e., weak and strong might be employed to achieve the same effect, as may the use of a reinforcement, e.g., through the selective incorporation of fibers and/or fabrics which limits the stretching of the balloon. The balloon sheets may also be welded or laminated in order to approximate monolithic sheets of nonuniform properties or thickness. In this manner, resistance to local stretching can be obtained which will alter inflated shape relative to shapes formed from uniform sheets (properties or geometry) of the same flat starting shapes.

Figure 3:
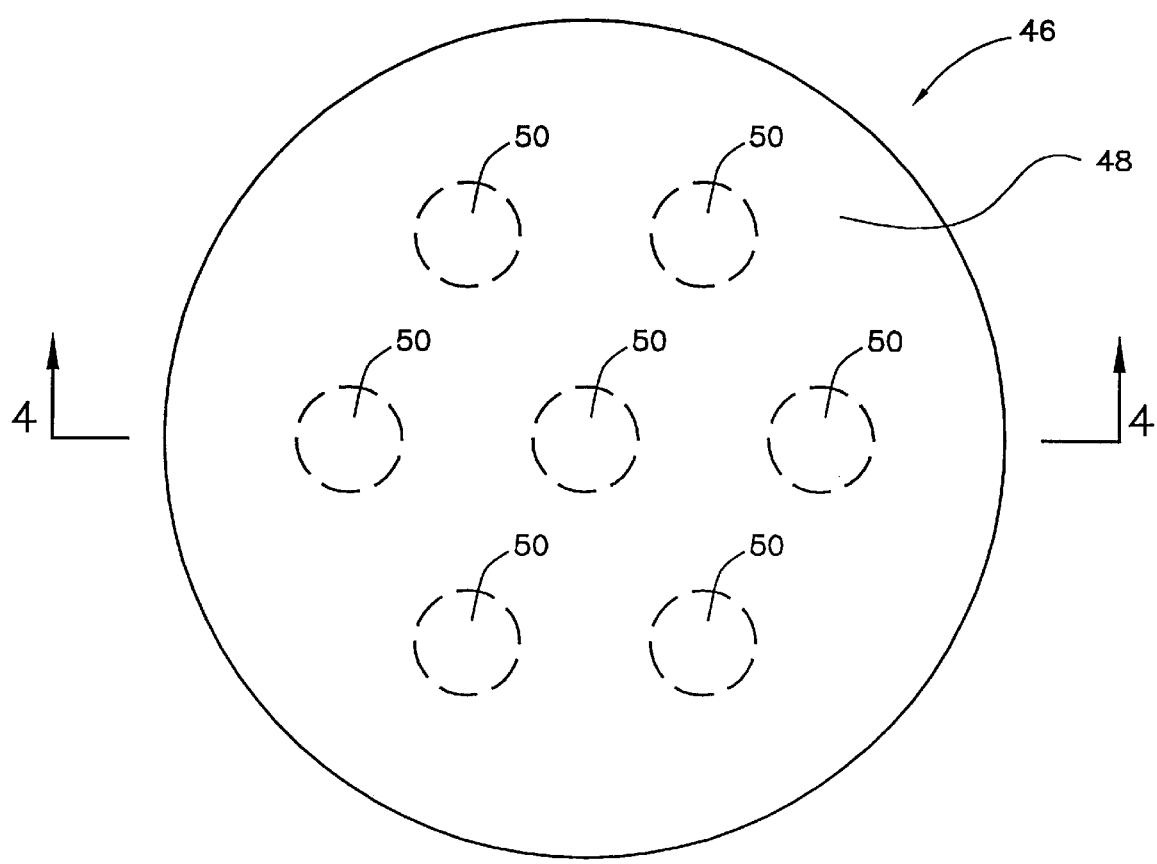
FIG. 3 is a top view of a preferred embodiment of a combination tissue dissector and expander in accordance with the present invention.
Figure 4:
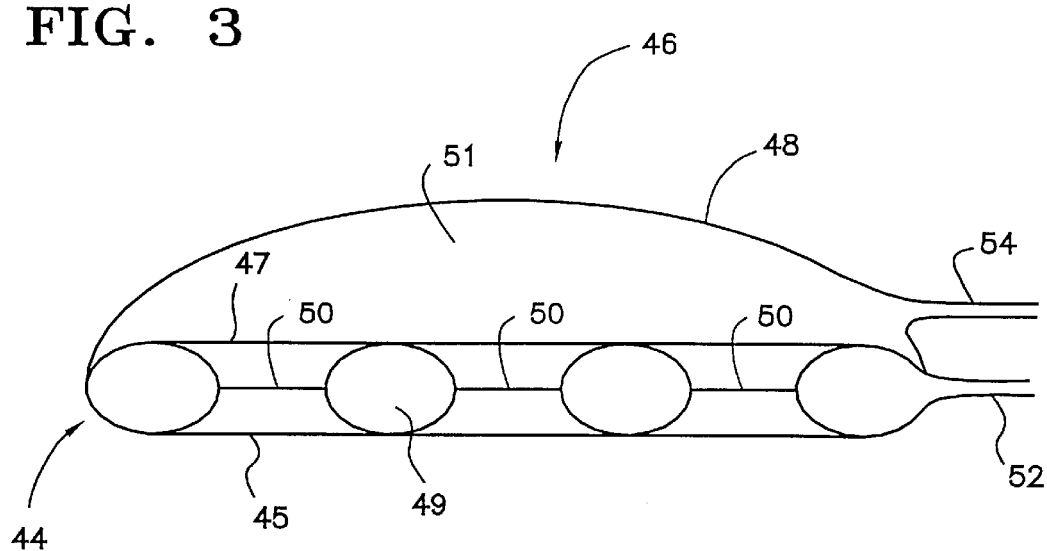
FIG. 4 is a cross-sectional view of the combination tissue dissector and expander illustrated in FIG. 3 taken along the lines labeled 4.

Compound constructions may also be employed, for example, as in FIGS. 3 and 4, where a structurally flat, "quilted" balloon is formed adjacent an open balloon. In such a construction, dissection may be carried out with either balloon to create the desired pocket or footprint, the structural balloon established, and then the expansion can progress from the footprint under controlled, periodic fluid increase.

In simple, one-balloon constructions, the fluid filler harness might be similar to those used for balloon dissectors. After dissection is complete, the harness fittings could be removed, and a filler port, complete with self-sealing membrane attached to the filler lumen, and the port implanted for the duration of the tissue expansion period. With compound constructions, either multiple filler lumens or a single lumen with suitable valving may be employed. If it is desired to gain fluid access to two distinct balloons in a compound structure after skin closure, then two implantable membrane ports may be utilized. If it is not required to access the dissection balloon, only one membrane injection port need be supplied, and the other lumen may be plugged or locked off.

In order to relieve the pressure needed for dissection, but still retain the relatively flat structure on one side at or below the tissue necrosis limit, the inflation pressure may be relieved in accordance with experimental results obtained which define the limits under which positive pressure in the balloon is retained even after significant fluid removal. Since the fluid pressure is the sum of the pressure generated by tissue elasticity and that from balloon elasticity, reducing the fluid pressure to the necrosis limit will assure that no tissue damage occurs. When the pressure is reduced, if the balloon is insufficiently rigid to maintain the flat shape additional stiffeners may be used. For example, longitudinal stiffeners, wire or strips, or the like, can be added in a parallel way which does not interfere with rolling or gathering of the deflated device in preparation for tunneling within the body to the expansion site.

Another useful construction includes placing an expander inside a dissector. In this construction, the dissected footprint may be greater than the footprint required for expansion, reducing the residual stress at the margins during expansion.

All constructions intended herein must be capable of rolling or compaction to facilitate placement from an incision site remote from the target expansion site (or at least adjacent) in a manner which will not promote tissue expander extrusion from the incision. Balloon covers, as disclosed in application Ser. No. 08/570,766, may be utilized to facilitate compaction of the balloon for tunneling.

It may be desirable to provide for balloon reuse, either to accommodate inspection/intervention between dissection and expansion, or to permit reuse of the device. If multiple insertions into the body are contemplated, means may be provided to reattach the tunneling member to the balloon if it is detached during any inflation step. A scope cover may be reinserted into the balloon to accommodate tunneling and visualization, and if a guide rod is used, it may be reattached. One reattachment method is to provide an external pocket at the distal tip of the balloon into which the end of the guide rod could be inserted repeatedly. New or reusable balloon covers may also be provided, either, for example, by reuse of a separable semi-rigid cover, or by a new but separate integral cover "sock" slipped over the rerolled balloon (or balloons in a compound construction).

A presently preferred balloon 46 for an exemplary combination dissector/expander is shown in FIGS. 3 and 4. FIG. 3 is a top view of the balloon 46 and illustrates welds 50 that are formed between the bottom and middle balloon layers 45 and 47, respectively, to form a semi-rigid inflatable base 44 for a purpose that will be explained below. As best seen in the cross-sectional view provided in FIG. 4, the combination dissector, sizer, and expander is preferably formed from three sheets of a material which is substantially inelastic over the range of pressures used to inflate the balloon. A thin sheet of polyurethane, exhibits suitable inelastic properties.

The bottom sheet 45 is bonded to the middle sheet 47 at the sheet outer margins by any suitable bonding system such as a heat sealing, for example. The sheets 45 and 47 define an interior space 49 therebetween which is in fluid communication with an inflation lumen 52 extending from the balloon 46. Additionally, the bottom and middle sheets 45 and 47 are bonded together at welds 50 at regularly spaced intervals over the entire surface area of the sheets 45 and 47. The inflation lumen 52 may be connected to a suitable balloon inflation source such as a syringe, for example. Although the balloon 46 may be inflated with air, saline solution is presently preferred.

Similarly, the upper balloon sheet 48 is bonded in a fluid-tight manner, such as by heat sealing, to the middle balloon sheet 47 to form an inflatable space 51 therebetween. The upper portion of the balloon 46 is inflated by introducing an inflation medium through the inflation lumen 54 into the interior space 51 of the balloon 46. The lower base portion 44 of the balloon 46 is semi-rigid and flat when inflated to facilitate operation of the balloon 46 as a tissue expander. The base 44 is made semi-rigid and flat in the manner of an air mattress, as shown in FIGS. 3 and 4, such that the base of the balloon 46 has a consistent footprint in the dissected pocket. The consistency or regularity of the footprint is desirable to prevent the dissected pocket from being laterally expanded at its margins when the device is used as a tissue expander after dissection has occurred. By providing a semi-rigid base, the expansion forces created by introducing the inflation fluid through the lumen 54 into the interior space 51 will be directed primarily in the anterior or Z-axis direction.

Several other techniques exist to restrict isotropic expansion of the balloon so that balloon expansion occurs primarily in the Z-axis direction, i.e., the direction perpendicular to the footprint of the combination device. In particular, a restraint may be provided by welding members inside the balloon which will tether the sheets of the balloon at a fixed dimension. This technique is more applicable to fabricated sheet balloons than to blow-molded or melt-form balloons. The tethering members may be baffles having finite length or may merely be intermediate welds between the facing sheets, as previously discussed.

In actual use, the balloon 46 may be rolled, folded, or otherwise compacted and carried by one of the tunneling devices illustrated in application Ser. No. 08/570,766, for example. (In plastic surgery applications, the reusable devices disclosed in application Ser. No. 08/570,766 are particularly desirable from the standpoint of cost). The combination device with the rolled, folded, or gathered balloon 46 is advanced bluntly to a desired location within the body. A tissue pocket may be created through dissection by introducing a saline solution inflation medium, such as through the lumen 54 into the interior space 51 defined by the top and middle balloon sheets 48 and 47, of the balloon 46. After the upper portion of the balloon 46 has been inflated to create the tissue pocket, a predetermined amount of inflation fluid may be withdrawn from the interior space 51 through the lumen 54 by suction to achieve a proper volume for long term expansion.

If it is necessary to further expand the dissected pocket, the base 44 of the balloon 46 is then inflated by introducing as inflation fluid through the lumen 52 into the interior space 49 defined by the middle and bottom balloon sheets 47 and 45, respectively. After the base 44 has been inflated to provide a semi-rigid and well-defined structure lying against the bottom or posterior side of the dissected space, the upper portion of the balloon 46 is again gradually inflated through lumen 54 observing the appropriate pressure regimes utilized in tissue expansion. The balloon 46 is then left in the dissected pocket over a period of time as a tissue expander. The internal pressure of the balloon 46 will need to be periodically adjusted as the tissue gradually expands over time. After the desired amount of tissue expansion has occurred, the balloon 46 may be removed by suctioning the inflation fluid from both the upper interior space 51 and the lower interior space 49 through lumens 54 and 52, respectively. The balloon 46 is then removed from the body, and a suitable prothesis is implanted.

The apparatus and methods disclosed above produce easy-to-use devices which have economic advantages over use of separate dissection and expansion devices used successively. Many combinations are possible, and the combinations described are intended only to be illustrative of the invention and not in any sense limiting. It will be understood by those skilled in the art that many changes in construction and widely differing embodiments and applications of the invention will suggest themselves without departing from the spirit and scope of the invention. For example, the combination devices herein described may be used in wide variety of applications where naturally occurring potential spaces or tissue or planes occur in the anatomy. Thus, the disclosure and the description herein are purely illustrative and are not intended to be in any sense limiting.

What is claimed is:

1. A combination dissector and expander comprising:

an inflatable bladder comprising first and second inflatable chambers, said first inflatable chamber defined between first and second sheets of material sealed together at their outer margins to form an inflatable space therebetween, said second chamber defined between said second sheet and a third sheet of material which are sealed together at their outer margins to form an inflatable space therebetween, and said second and third sheets of material further bonded together at spaced apart intervals over their respective surfaces.

2. The combination dissector and expander of claim 1 wherein said first, second, and third sheets of material are a non-elastomeric material.

3. A combination dissector and expander comprising:

an inflatable bladder comprising first and second inflatable chambers;

said second inflatable chamber comprising stiffeners being aligned in parallel, said stiffeners configured to make the second inflatable chamber semi-rigid and relatively flat in an inflated state.

4. The combination dissector and expander of claim 3 wherein said stiffeners comprise wires.

5. The combination dissector and expander of claim 3 wherein said stiffeners comprise strips of stiffening material.

6. The combination dissector and expander of claim 3 wherein said stiffeners comprise tethering members.

7. The combination dissector and expander of claim 3 wherein said stiffeners comprise baffles.

* * * * *